(12) United States Patent
Jung

(10) Patent No.: US 9,945,340 B2
(45) Date of Patent: Apr. 17, 2018

(54) DARK CURRENT EXCESS PREVENTION METHOD IN TELEMATICS TERMINAL AND APPARATUS THEREFOR

(71) Applicant: Hyundai Motor Company, Seoul (KR)

(72) Inventor: Jae Hoon Jung, Seoul (KR)

(73) Assignee: Hyundai Motor Company, Seoul (KR)

( * ) Notice: Subject to any disclaimer, the term of this patent is extended or adjusted under 35 U.S.C. 154(b) by 16 days.

(21) Appl. No.: 14/945,386

(22) Filed: Nov. 18, 2015

(65) Prior Publication Data

US 2017/0074916 A1 Mar. 16, 2017

(30) Foreign Application Priority Data

Sep. 11, 2015 (KR) ........................ 10-2015-0129032

(51) Int. Cl.
*F02N 11/08* (2006.01)
*G07C 5/08* (2006.01)
(Continued)

(52) U.S. Cl.
CPC ........ *F02N 11/0807* (2013.01); *G07C 5/0808* (2013.01); *B60L 1/00* (2013.01); *B60N 2/0232* (2013.01); *B60R 16/033* (2013.01); *G01N 33/0065* (2013.01); *G01R 31/3606* (2013.01); *G01R 31/3651* (2013.01); *G06F 7/00* (2013.01); *G08B 1/08* (2013.01); *G08B 17/10* (2013.01); *H02H 3/08* (2013.01); *H02H 3/087* (2013.01);
(Continued)

(58) Field of Classification Search
CPC ......... G06F 7/00; G06F 1/3212; H02H 3/087; H02H 7/08; H02H 3/08; H02J 7/00; H02J 7/1423; H02J 7/0021; B60R 16/033; B60L 1/00; B60N 2/0232; G01N 33/0065; G01R 31/3606; G01R 31/3651; F02N 11/0807; G07C 5/0808; G08B 1/08; G08B 25/009; G08B 29/26; G08B 17/10; G08B 21/182; G08B 25/007; G08B 25/10; G08B 17/11; G08B 27/005; H04B 1/401; H04B 1/69; F24F 7/007; F24F 11/0017; H01M 10/48

See application file for complete search history.

(56) References Cited

U.S. PATENT DOCUMENTS

2006/0038532 A1* 2/2006 Taniguchi ............. H02J 7/1423
 320/103
2011/0228429 A1* 9/2011 Ueta .................... B60N 2/0232
 361/31

(Continued)

FOREIGN PATENT DOCUMENTS

JP 2008-260384 A 10/2008
JP 2010-083154 A 4/2010
(Continued)

*Primary Examiner* — Behrang Badii
(74) *Attorney, Agent, or Firm* — Mintz Levin Cohn Ferris Glovsky and Popeo, P.C.; Peter F. Corless

(57) ABSTRACT

A dark current excess prevention method in a telematics terminal installed in a vehicle includes: calculating a current consumption amount up to a present time upon sensing a transmission operation in a sleep mode; determining whether the calculated current consumption amount exceeds a predetermined dark current reference value; and determining that a dark current is exceeded when the calculated current consumption amount exceeds the dark current reference value.

20 Claims, 5 Drawing Sheets

(51) Int. Cl.
  *H02H 3/087* (2006.01)
  *H02H 3/20* (2006.01)
  *H02J 7/00* (2006.01)
  *G01R 31/36* (2006.01)
  *H02J 7/16* (2006.01)
  *H02H 3/08* (2006.01)
  *G08B 1/08* (2006.01)
  *B60R 16/033* (2006.01)
  *G01N 33/00* (2006.01)
  *B60L 1/00* (2006.01)
  *H02H 7/08* (2006.01)
  *G08B 17/10* (2006.01)
  *H02J 7/04* (2006.01)
  *G06F 7/00* (2006.01)
  *B60N 2/02* (2006.01)
  *H02J 7/14* (2006.01)

(52) U.S. Cl.
  CPC .................. *H02H 3/20* (2013.01); *H02H 7/08* (2013.01); *H02J 7/00* (2013.01); *H02J 7/04* (2013.01); *H02J 7/1423* (2013.01); *H02J 7/16* (2013.01)

(56) References Cited

U.S. PATENT DOCUMENTS

| | | | | |
|---|---|---|---|---|
| 2011/0270490 A1* | 11/2011 | Katou | ...................... | B60L 1/00 701/36 |
| 2013/0067256 A1* | 3/2013 | Shiraishi | ............ | G01R 31/3606 713/320 |
| 2014/0320295 A1* | 10/2014 | Kates | ................. | G01N 33/0065 340/628 |
| 2017/0106820 A1* | 4/2017 | Maruyama | ............ | B60R 16/033 |

FOREIGN PATENT DOCUMENTS

| | | |
|---|---|---|
| JP | 5141424 B2 | 2/2013 |
| JP | 2014-140268 A | 7/2014 |
| JP | 2015-093634 A | 5/2015 |
| KR | 10-0765890 B1 | 10/2007 |
| KR | 10-2009-0111948 A | 10/2009 |
| KR | 10-2015-0044201 A | 4/2015 |

* cited by examiner

FIG. 6

| Threshold value compensation coefficient | Temperature | Compensated dark current threshold value | Note |
|---|---|---|---|
| 1.1 | Temperature<0℃ | 1.1*threshold | Transition to protection mode when consumption current exceeds 110% of allowed dark current |
| 1 | 0℃ ≤ temperature≤40℃ | 1.0*threshold | Transition to protection mode when consumption current exceeds 100% of allowed dark current |
| 0.9 | Temperature>40℃ | 0.9*threshold | Transition to protection mode when consumption current exceeds 90% of allowed dark current |

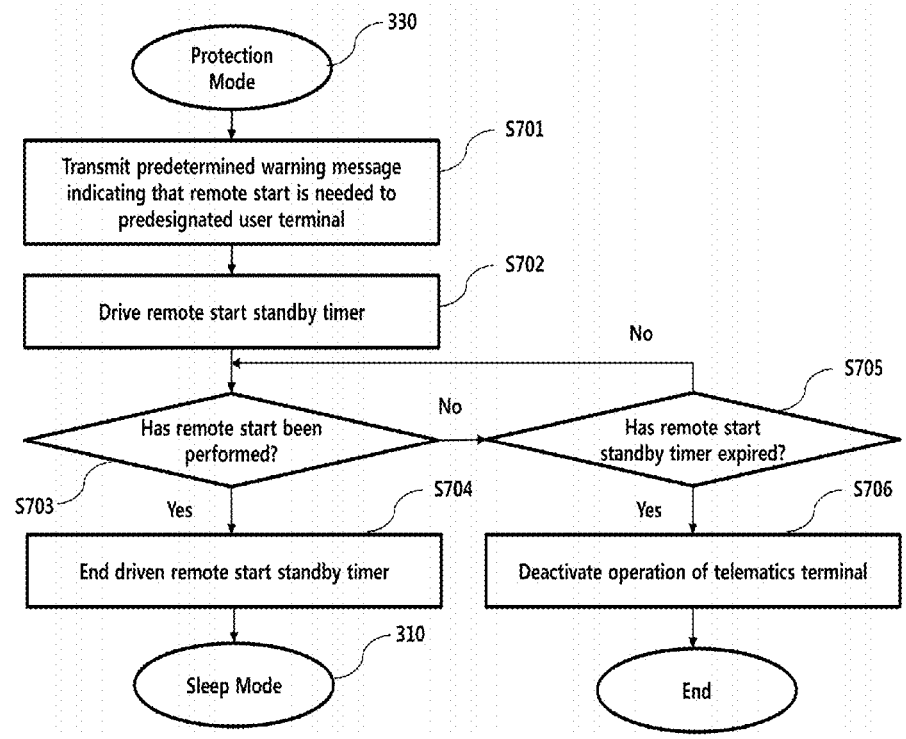

FIG. 7

DARK CURRENT EXCESS PREVENTION METHOD IN TELEMATICS TERMINAL AND APPARATUS THEREFOR

CROSS-REFERENCE TO RELATED APPLICATION

This application claims the benefit of and priority to Korean Patent Application No. 10-2015-0129032, filed on Sep. 11, 2015, which is hereby incorporated by reference as if fully set forth herein.

BACKGROUND OF THE DISCLOSURE

Technical Field

The present disclosure relates generally to a dark current excess prevention method and, more particularly, to a dark current excess prevention method in a telematics terminal and an apparatus therefor that can judge whether a dark current is exceeded based on a real-time consumption current.

Discussion of the Related Art

Generally, electronic devices immediately operate when they are powered on after being powered off. To maintain a basic operation of an electronic device, a minimum current is supplied to various components of the electronic device. Such a current is called a dark current.

Meanwhile, if the dark current of an electronic device installed in a vehicle is excessively high, since an unnecessary battery power is consumed, the battery of the vehicle may be discharged, and malfunction of the electronic device may be caused. Therefore, proper handling for the dark current is needed.

Korean Laid-open Patent No. 10-2015-0044201 ("Apparatus and method for cutting off current consumption of a battery used in vehicle") discloses a method for calculating a dark current consumption value for all electronic devices installed in a vehicle and cutting off power supply to the electronic devices or generating and displaying a predetermined alarm when the entire dark current consumption value exceeds a predetermined reference value and a battery charge is less than a threshold value. Although the above dark current measurement method enables a vehicle user to identify that the vehicle is abnormal through the displayed alarm, a limitation exists when attempting to identify which electronic device has an error.

Similarly, Korean Patent Publication No. 10-2009-0111948 ("Electronic device diagnosis information provision method of vehicle") discloses a method for measuring a dark current of an individual electronic device in a vehicle and providing an indication representing that the electronic device has an error to a driver through a screen unit installed in the vehicle when the measured dark current is higher than a reference value. However, simple determination as to whether an electronic device has an error only by comparing the measured dark current of each electronic device with predefined reference value has been problematic in that current dissipation patterns for various electronic devices of the vehicle cannot be considered.

In a conventional vehicle remote control operation including, for example, a remote start operation or an air-conditioning control operation, a modem of a vehicle telematics terminal needs to receive a remote control message in a sleep mode from an external user terminal (e.g., a smartphone). Since only a reception operation is performed in the sleep mode of a normal environment, an average current consumption amount is predictable. However, in a situation in which a sleep mode and an active mode are repeatedly switched, for example, the average current consumption amount could not be predicted because a transmission operation is additionally performed.

SUMMARY OF THE DISCLOSURE

Accordingly, the present disclosure is directed to a dark current excess prevention method in a telematics terminal and an apparatus therefor that substantially obviate one or more problems due to limitations and disadvantages of the related art.

An object of the present disclosure is to provide a dark current excess prevention method in a telematics terminal and an apparatus therefor that can accurately judge whether a dark current is exceeded by calculating a consumption power in the telematics terminal in real-time. Another object of the present disclosure is to provide a dark current excess prevention method in a telematics terminal and an apparatus therefor that can accurately judge whether a dark current is exceeded by calculating a consumption power in real-time according to a vehicle temperature condition.

The technical objects that can be achieved through the present disclosure are not limited to what has been particularly described hereinabove and other technical objects not described herein will be more clearly understood by persons skilled in the art from the following detailed description. Additional advantages, objects, and features of the disclosure will be set forth in part in the description which follows and in part will become apparent to those having ordinary skill in the art upon examination of the following or may be learned from practice of the disclosure. The objectives and other advantages of the disclosure may be realized and attained by the structure particularly pointed out in the written description and claims hereof as well as the appended drawings.

To achieve these objects and other advantages and in accordance with the purpose of the disclosure, as embodied and broadly described herein, a dark current excess prevention method in a telematics terminal installed in a vehicle includes: calculating a current consumption amount up to a present time upon sensing a transmission operation in a sleep mode; determining whether the calculated current consumption amount exceeds a predetermined dark current reference value; and determining that a dark current is exceeded when the calculated current consumption amount exceeds the dark current reference value.

The current consumption amount may be calculated by adding a current amount consumed for a reception operation up to the present time after transition to the sleep mode and a current amount consumed for a transmission operation up to the present time after the transition to the sleep mode.

The current amount consumed for the reception operation may be calculated based on a precalculated average consumption current for the reception operation.

The current amount consumed for the transmission operation may be calculated by multiplying a number of transmission operations after the transition to the sleep mode by an average current amount consumed during one transmission operation.

The dark current excess prevention method may further include: transitioning to a protection mode when it is determined that the dark current is exceeded; and transmitting a predetermined warning message indicating that remote start is needed to a predesignated user terminal in the protection mode.

The dark current excess prevention method may further include: driving a predetermined remote start standby timer after transmitting the warning message. An operation of the telematics terminal may be stopped when a remote start command is not received from the user terminal before expiry of the remote start standby timer.

The dark current excess prevention method may further include: performing the remote start upon receiving the remote start command. The transition to the sleep mode may be performed when the remote start is completed.

The dark current excess prevention method may further include: sensing a temperature of the vehicle. The dark current reference value may be dynamically compensated for based on the sensed temperature of the vehicle.

The dark current reference value may decrease when the sensed temperature of the vehicle increases, and the dark current reference value may increase when the sensed temperature of the vehicle decreases.

The dark current excess prevention method may further include: calculating a battery charge level of the vehicle. The dark current reference value may be determined based on the battery charge level of the vehicle.

Furthermore, in accordance with embodiments of the present disclosure, a dark current excess prevention apparatus includes: a communication unit configured to transmit and receive a packet; and a controller configured to calculate a current consumption amount up to a present time upon sensing a transmission operation in a sleep mode, determine whether the calculated current consumption amount exceeds a predetermined dark current reference value, and determine that a dark current is exceeded when the calculated current consumption amount exceeds the dark current reference value.

The current consumption amount may be calculated by adding a current amount consumed for a reception operation up to the present time after transition to the sleep mode and a current amount consumed for a transmission operation up to the present time after the transition to the sleep mode.

The current amount consumed for the reception operation may be calculated based on a precalculated average consumption current for the reception operation.

The current amount consumed for the transmission operation may be calculated by multiplying a number of transmission operations after the transition to the sleep mode by an average current amount consumed during one transmission operation.

The controller may be further configured to transition to a protection mode when it is determined that the dark current is exceeded and transmit a predetermined warning message indicating that remote start is needed to a predesignated user terminal in the protection mode.

The dark current excess prevention apparatus may further include: a timer driving a predetermined remote start standby timer after the warning message is transmitted. The controller may be further configured to stop an operation of a telematics terminal when a remote start command is not received from the user terminal before expiry of the remote start standby timer.

The controller may be further configured to initiate performance of the remote start upon receiving the remote start command and transition to the sleep mode upon completing remote start.

The dark current excess prevention apparatus may further include: a temperature sensor sensing a temperature of a vehicle. The controller may be further configured to dynamically compensate for the dark current reference value based on the sensed temperature of the vehicle.

The dark current reference value may decrease when the sensed temperature of the vehicle increases and the dark current reference value may increase when the sensed temperature of the vehicle decreases.

The dark current excess prevention apparatus may further include: a charge level sensor calculating a battery charge level of a vehicle in which a telematics terminal is installed. The controller may be further configured to determine the dark current reference value based on the battery charge level of the vehicle.

Furthermore, according to embodiments of the present disclosure, a non-transitory computer readable medium containing program instructions for performing a dark current excess prevention method in a telematics terminal installed in a vehicle includes: program instructions that calculate a current consumption amount up to a present time upon sensing a transmission operation in a sleep mode; program instructions that determine whether the calculated current consumption amount exceeds a predetermined dark current reference value; and program instructions that determine that a dark current is exceeded when the calculated current consumption amount exceeds the dark current reference value.

The above technical solutions are merely some parts of the embodiments of the present disclosure, and various embodiments into which the technical features of the present disclosure are incorporated can be derived and understood by persons skilled in the art from the following detailed description of the present disclosure.

BRIEF DESCRIPTION OF THE DRAWINGS

The accompanying drawings, which are included to provide a further understanding of the disclosure and are incorporated in and constitute a part of this application, illustrate embodiments of the disclosure and together with the description serve to explain the principle of the disclosure. In the drawings:

FIG. 6 is a dark current threshold value compensation table for explaining a dark current threshold value compensation method in accordance with a vehicle temperature according to embodiments of the present disclosure; and FIG. 7 is a flowchart for explaining an operation of a dark current excess prevention apparatus in a protection mode according to embodiments of the present disclosure.

DETAILED DESCRIPTION OF THE DISCLOSURE

Figure 1:
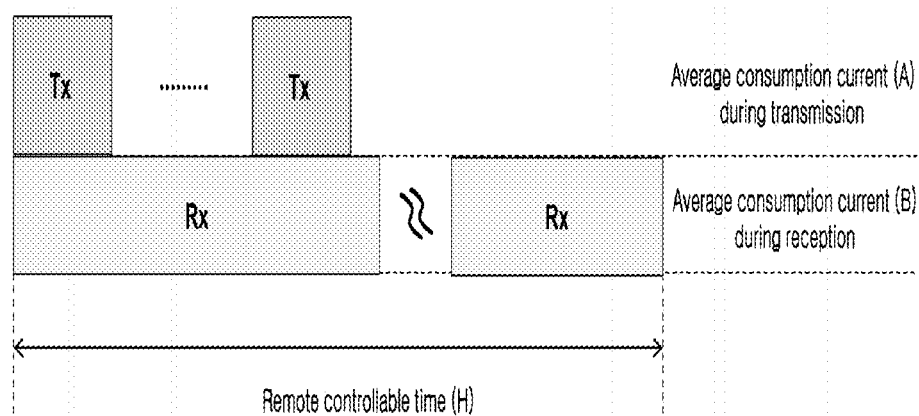
FIG. 1 is a diagram for explaining a dark current excess determination method in a telematics terminal according to embodiments of the present disclosure.

Hereinafter, an apparatus and various methods to which embodiments of the present disclosure are applied will be described in detail with reference to the attached drawings.

Suffixes "module" and "unit" with respect to constituent elements used in the following description are given only in consideration of facilitation of description and do not have distinct meanings or functions.

In the description below, although all of the components of the embodiments of the present disclosure may have been explained as assembled or operatively connected as a unit, the present disclosure is not limited to such embodiments. Rather, within some embodiments of the present disclosure, the respective components are selectively and operatively combined in any number of ways. Each of the components is capable of being implemented alone in hardware or combined in part or as a whole and implemented in a computer program having program modules executing functions of the hardware equivalents. Code or code segments to constitute such a program are understood by a person skilled in the art. The computer program is stored in a computer readable media, which in operation realizes the embodiments of the present disclosure. The computer readable media includes magnetic recording media, optical recording media or carrier wave media, in some embodiments.

In addition, terms such as "include", "comprise", and "have" are to be interpreted by default as inclusive or open rather than exclusive or closed unless expressly defined to the contrary. All the terms that are technical, scientific or otherwise agree with the meanings as understood by a person skilled in the art unless defined to the contrary. Common terms as found in dictionaries are interpreted in the context of the related technical writings not too ideally or impractically unless the present disclosure expressly defines them so.

Additionally, in describing the components of the present disclosure, terms like first, second, A, B, (a), and (b) are used. These terms are solely for the purpose of differentiating one component from another, and one of ordinary skill would understand that the terms do not to imply or suggest the substances, order or sequence of the components. If a component is described as "connected", "coupled", or "linked" to another component, one of ordinary skill in the art would understand that the components are not necessarily directly "connected", "coupled", or "linked" but also are indirectly "connected", "coupled", or "linked" via a third component.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g., fuels derived from resources other than petroleum). As referred to herein, a hybrid vehicle is a vehicle that has two or more sources of power, for example both gasoline-powered and electric-powered vehicles.

Additionally, it is understood that one or more of the below methods, or aspects thereof, may be executed by at least one controller. The term "controller" may refer to a hardware device that includes a memory and a processor. The memory is configured to store program instructions, and the processor is specifically programmed to execute the program instructions to perform one or more processes which are described further below. Moreover, it is understood that the below methods may be executed by an apparatus comprising the controller in conjunction with one or more other components, as would be appreciated by a person of ordinary skill in the art.

Furthermore, the controller of the present disclosure may be embodied as non-transitory computer readable media on a computer readable medium containing executable program instructions executed by a processor, controller or the like. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed in network coupled computer systems so that the computer readable media is stored and executed in a distributed fashion, e.g., by a telematics server or a Controller Area Network (CAN).

Referring now to the disclosed embodiments, FIG. 1 is a diagram for explaining a dark current excess determination method in a telematics terminal according to embodiments of the present disclosure.

Prior to description of a dark current excess prevention method according to the present disclosure, a conventional dark current excess prevention method will now be described with reference to FIG. 1.

According to the conventional method depicted in FIG. 1, a maximum number of transmissions, $T_{max}$, for a predetermined remote controllable time H is calculated, and if the number of transmissions in a telematics terminal reaches the maximum number of transmissions prior to expiry of the remote controllable time H, the telematics terminal determines that a dark current is exceeded. As an example, the remote controllable time H may be determined based on, without being limited to, at least one of capacity of a battery included in a vehicle, a current battery charge, and an average dark current consumption amount of electronic devices in the vehicle.

Herein, the maximum number of transmissions, $T_{max}$, may be calculated by dividing, by an average consumption current A during one transmission operation, a value obtained by subtracting a current consumption amount (H*B) for a reception operation for the remote controllable time H (where B indicates an average consumption current during a reception operation) from an allowed dark current amount C. This may be expressed by $T_{max}=(C-H*B)/A$.

If it is determined that the dark current is exceeded, the telematics terminal deactivates operation thereof.

However, according to the conventional method, since the maximum number of transmissions, $T_{max}$, is calculated based on the worst case, i.e., the case in which a reception operation continues for the remote controllable time H, whether the dark current is exceeded cannot be accurately determined.

The dark current excess determination method according to embodiments of the present disclosure can be accurately and rapidly performed by determining whether a current consumed up to now exceeds an allowed dark current whenever a transmission operation occurs. In addition, the dark current excess prevention method according to embodiments of the present disclosure can more accurately judge whether the dark current is exceeded by adaptively compensating for a power consumption amount according to temperature of a vehicle. Additionally, the dark current excess prevention method according to embodiments of the present disclosure can prevent a battery from being discharged and can continue to maintain operation of a telematics terminal by requesting that a predesignated user terminal perform remote start upon judging that a dark current is exceeded.

Hereinafter, dark current excess prevention methods in a telematics terminal and an apparatus therefor according to embodiments of the present disclosure will be described in detail with reference to FIGS. 2 to 7.

Figure 2:
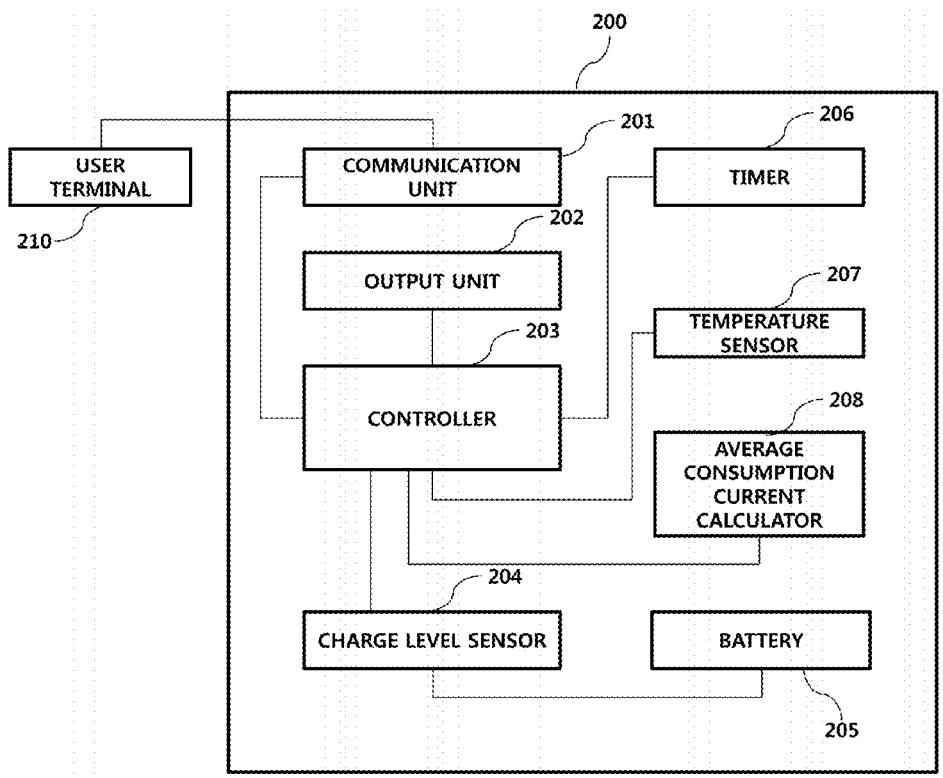
FIG. 2 is a block diagram of a dark current excess prevention apparatus according to embodiments of the present disclosure.

FIG. 2 is a block diagram of a dark current excess prevention apparatus according to embodiments of the present disclosure.

As shown in FIG. 2, the dark current excess prevention apparatus 200 may include a communication unit 201, an output unit 202, a controller 203, a charge level sensor 204, a battery 205, a timer 206, a temperature sensor 207, and an average consumption current calculator 208. The above components of the dark current excess prevention apparatus 200 are non-essential. Accordingly, it should be noted that the dark current excess prevention apparatus 200 may include a greater or smaller number of components than those mentioned above.

The dark current excess prevention apparatus 200 according to embodiments of the present disclosure may be installed in a telematics terminal. However, this is purely exemplary and it should be noted that some of the components of the dark current excess prevention apparatus 200 may be installed at the outside of the telematics terminal so as to be linked to the dark current excess prevention apparatus 200.

The communication unit 201 may include a wired or wireless modem for telematics communication. The dark current excess prevention apparatus 200 may exchange various information (i.e., packets) and control signals with a user terminal 210 through the communication unit 201.

The communication unit 201 may transmit packets received from the controller 203 to the user terminal 210 or a telematics server (not illustrated) according to types of the packets or transmit packets received from the user terminal 210 or the telematics servicer to the controller 203.

The output unit 202 may include at least one of a display means such as a liquid crystal display (LCD), a sound output means such as a speaker, and an alarm means such as a light emitting diode (LED)/vibration module. As an example, the output unit 202 may display a predetermined warning message indicating that a dark current excess phenomenon has occurred according to a control signal of the controller 203. The output unit 202 may also output a battery warning message or a vehicle start suggestion message according to the control signal of the controller 203.

The controller 203 may control overall operation of the dark current excess prevention apparatus 200. Operation of the controller 203 will be more apparent through below description of other modules.

The charge level sensor 204 may sense a current charge level of the battery 205 and inform the controller 203 of the charge level of the battery 205. If the current charge level of the battery 205 drops below a predetermined reference level, the charge level sensor 204 may provide a predetermined warning message to the controller 203.

The timer 206 may provide various timing information and timer functions necessary for operation of the dark current excess prevention apparatus 200. As an example, if it is determined that a consumption current amount up to now exceeds a dark current, the controller 203 may transmit a predetermined warning message indicating that remote start is needed to the user terminal 210 through the communication unit 201. Thereafter, the controller 203 may request that the timer 206 operate a predetermined remote start standby timer. If the remote start standby timer expires, the timer 206 may generate a predetermined timer expiry event signal and, if the timer expiry event is sensed, the controller 203 may deactivate the telematics terminal.

The temperature sensor 207 may sense an internal or external temperature of a vehicle and provide the sensed temperature to the controller 203. As an example, the controller 203 may dynamically compensate for an available dark current amount based on information about the temperature of the vehicle received from the temperature sensor 207. Herein, the available dark current amount may be compensated for in such a manner that the available dark current amount decreases as the temperature increases and the available dark current amount increases as the temperature decreases.

The average consumption current calculator 208 may calculate an average current consumption amount per unit time of the telematics terminal. Herein, the average current consumption amount may include an average current consumption amount dissipated for a transmission operation for a unit time and an average current consumption amount dissipated for a reception operation for a unit time. In addition, the average consumption current calculator 208 may calculate an average current amount dissipated during one transmission operation.

The controller 203 may calculate a consumption current amount up to now whenever a transmission operation occurs. Herein, the consumption current amount c up to now may be calculated by Equation (1) below.

$$c = h*B + T_{count}*A \qquad \text{Equation (1)}$$

Here, h denotes an expiry time up to now after the controller 203 enters a sleep mode, B denotes an average current consumed during a reception operation, $T_{count}$ denotes the number of transmissions accumulated up to now, and A denotes an average current amount consumed during one transmission operation.

In this case, the controller 203 may compare the consumption current amount c up to the now with an available dark current amount Threshold to determine whether a dark current excess phenomenon has occurred.

Furthermore, according to embodiments of the present disclosure, the controller 203 may calculate a compensated dark current amount Threshold' by compensating for the available dark current amount Threshold based on the information about the temperature of the vehicle collected from the temperature sensor 207.

Next, the controller 203 may compare the calculated consumption current amount c up to now with the compensated available dark current Threshold' to determine whether the dark current excess phenomenon has occurred.

If it is judged that the dark current is exceeded, the controller 203 may transition to a protection mode to transmit a predetermined warning message indicating that remote start is needed to a predesignated user terminal.

Upon receiving a predetermined remote start command from the user terminal within a predetermined time after transmitting the warning message, the controller 203 may control remote start and then transition to the sleep mode from the protection mode.

If the remote start command is not received from the user terminal even after expiry of the predetermined time after the warning message is transmitted, the controller 203 may deactivate operation of the telematics terminal.

Figure 3:
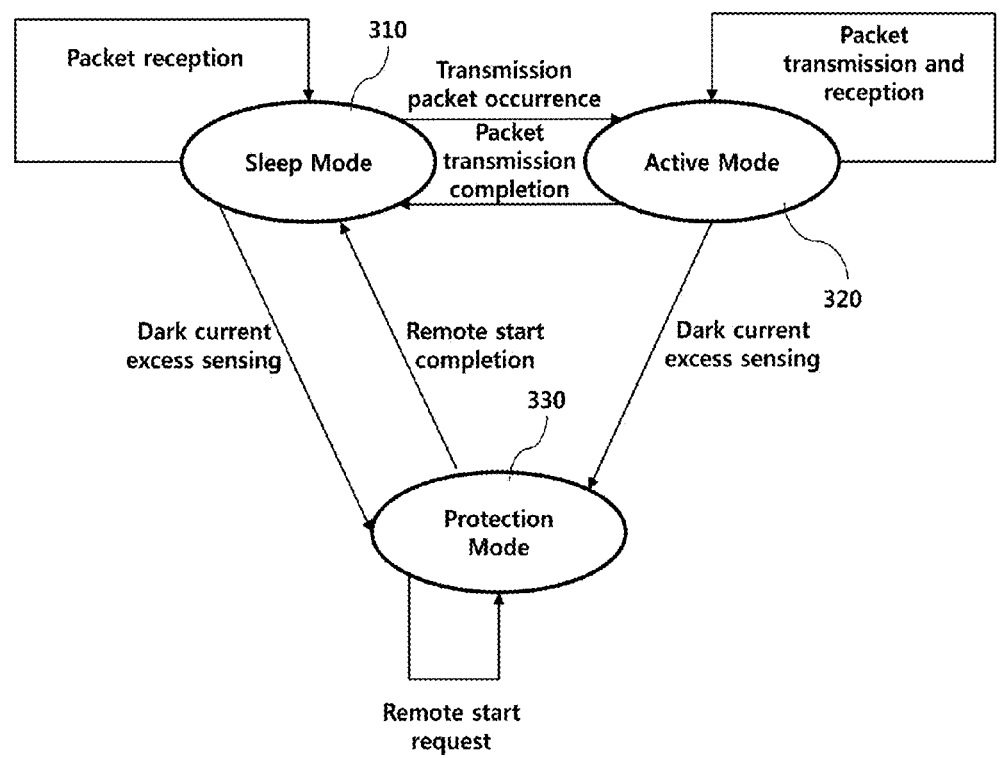
FIG. 3 is a diagram for explaining state transition in a dark current excess prevention apparatus according to embodiments of the present disclosure.

FIG. 3 is a diagram for explaining state transition in a dark current excess prevention apparatus according to embodiments of the present disclosure.

As shown in FIG. 3, the state of the dark current excess prevention apparatus may broadly include a sleep mode 310, an active mode 320, and a protection mode 330.

In the sleep mode 310, the dark current excess prevention apparatus may receive a packet from an external device such as a telematics server or a user terminal.

If there is a packet to be transmitted to an external device in the sleep mode 310, the dark current excess prevention apparatus may transition to the active mode 320. In the active mode 320, the dark current excess prevention apparatus may perform a packet transmission operation as well as a packet reception operation.

Upon completion of the packet transmission operation, the dark current excess prevention apparatus may again transition to the sleep mode 310 from the active mode 320.

Upon sensing that a dark current is exceeded in the sleep mode 310 or the active mode 320, the dark current excess prevention apparatus may transition to the protection mode 330. In the protection mode 330, the dark current excess prevention apparatus may transmit a predetermined warning message indicating that remote start is needed to a predesignated user terminal. Upon receiving a remote start command from the user terminal, the dark current excess prevention apparatus may perform remote start and then transition again to the sleep mode 310.

Figure 4:
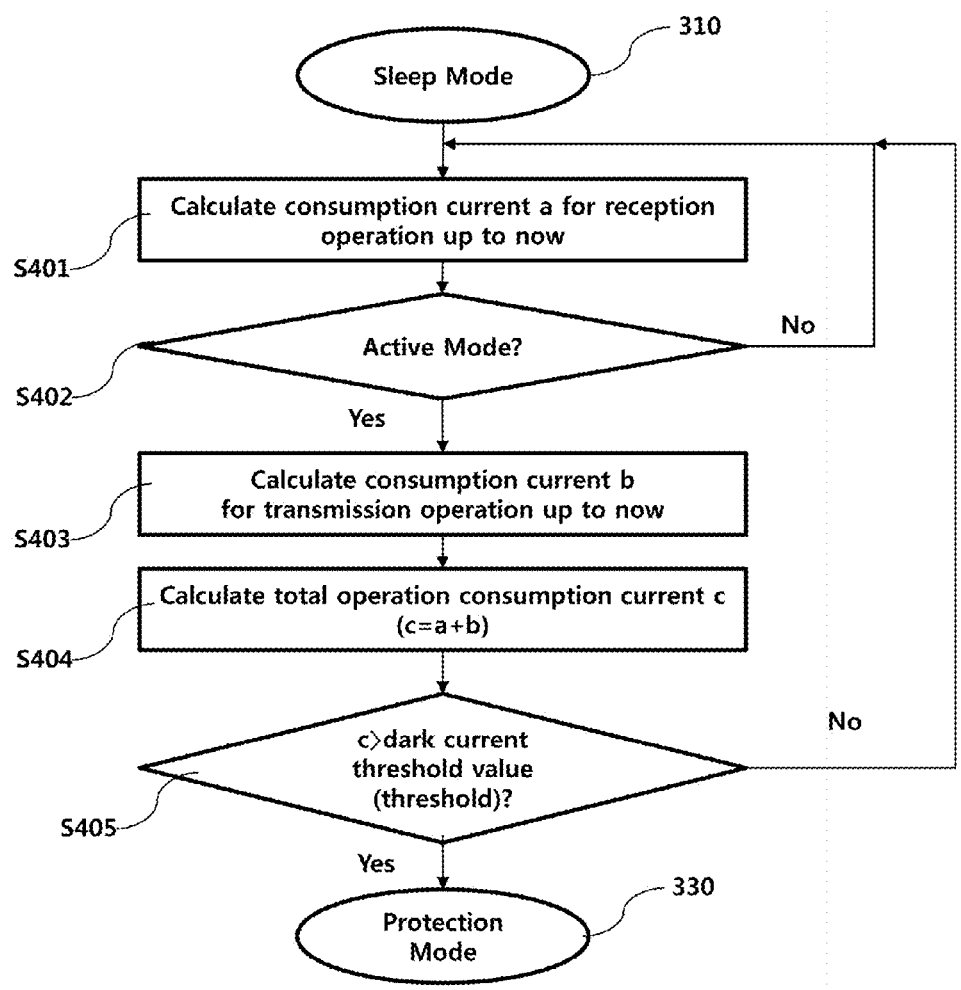
FIG. 4 is a flowchart for explaining a dark current excess prevention method in a telematics terminal according to embodiments of the present disclosure.

FIG. 4 is a flowchart for explaining a dark current excess prevention method in a telematics terminal according to embodiments of the present disclosure.

As shown in FIG. 4, a dark current excess prevention apparatus may calculate a consumption current a for a reception operation up to now in the sleep mode 310 (step S401).

The dark current excess prevention apparatus may monitor whether there is a packet to be transmitted in the sleep mode 310 (step S402). That is, the dark current excess prevention apparatus may check whether the state thereof transitions to an active mode 320 for packet transmission.

As a result if the state of the dark current excess prevention apparatus transitions to the active mode 320, the dark current excess prevention apparatus may calculate a consumption current b for a transmission operation up to now and add the consumption current a for the reception operation and the consumption current b for the transmission operation up to now, thereby calculating a total operation consumption current c (step S403 and step S404).

Next, the dark current excess prevention apparatus may check whether the total operation consumption current c exceeds a preset dark current threshold value Threshold (step S405).

If the total operation consumption current c exceeds the preset dark current threshold value Threshold, the state of the dark current excess prevention apparatus may transition to the protection mode 330.

In step 402, if the state of the dark current excess prevention apparatus does not the active mode 320, the dark current excess prevention apparatus may return to step 401 to calculate the consumption current a for the reception operation up to now.

Additionally, in step S405, if the total operation consumption current c does not exceed the preset dark current threshold value Threshold, the dark current excess prevention apparatus may return to step 401 to calculate the consumption current a for the reception operation up to now.

Figure 5:
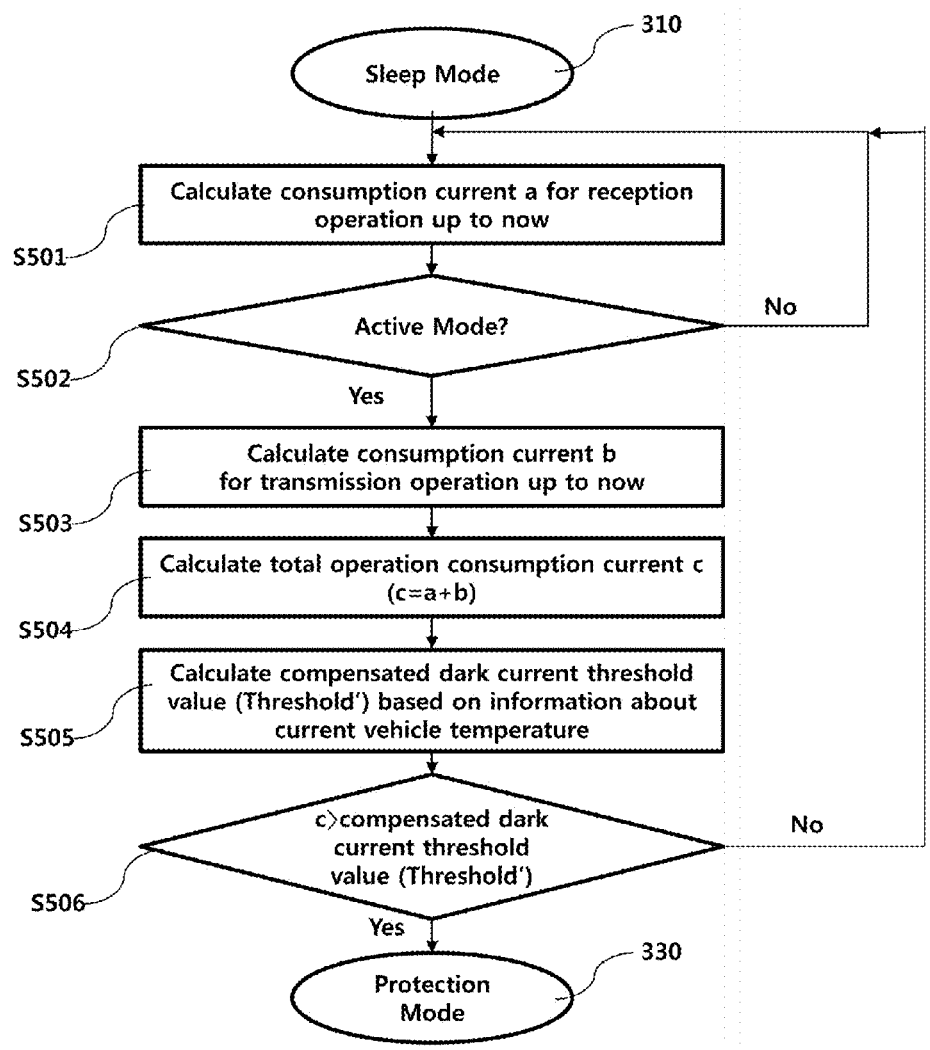
FIG. 5 is a flowchart for explaining a dark current excess prevention method in a telematics terminal according to embodiments of the present disclosure.

FIG. 5 is a flowchart for explaining a dark current excess prevention method in a telematics terminal according to embodiments of the present disclosure.

As shown in FIG. 5, the dark current excess prevention apparatus may calculate a consumption current a for a reception operation up to now in the sleep mode 310 (step S501).

The dark current excess prevention apparatus may monitor whether there is a packet to be transmitted in the sleep mode 310 (step S502). That is, the dark current excess prevention apparatus may check whether the state thereof transitions to an active mode 320 for packet transmission.

As a result of check, if the state of the dark current excess prevention apparatus transitions to the active mode 320, the dark current excess prevention apparatus may calculate a consumption current b for a transmission operation up to now and add the consumption current a for the reception operation and the consumption current b for the transmission operation up to now, thereby calculating a total operation consumption current c (step S503 and step S504).

The dark current excess prevention apparatus may calculate a compensated dark current threshold value Threshold' based on information about a current vehicle temperature (step S505).

Next, the dark current excess prevention apparatus may check whether the total operation consumption current c exceeds the compensated dark current threshold value Threshold' (step S506).

If the total operation consumption current c exceeds the compensated dark current threshold value Threshold', the state of the dark current excess prevention apparatus may transition to the protection mode 330.

In step 502, if the state of the dark current excess prevention apparatus does not transition to the active mode 320, the dark current excess prevention apparatus may return to step 501 to calculate the consumption current a for the reception operation up to now.

Additionally, in step S506, if the total operation consumption current c does not exceed the compensated dark current threshold value Threshold', the dark current excess prevention apparatus may return to step 501 to calculate the consumption current a for the reception operation up to now.

In the embodiments of FIGS. 4 and 5, although the dark current excess prevention apparatus calculates the current amount consumed for the reception operation up to now when the apparatus enters the sleep mode 310, this is purely exemplary. Furthermore, according to embodiments of the present disclosure, it should be noted that, if the dark current excess prevention apparatus transitions to the active mode 320 from the sleep mode 310, the dark current excess prevention apparatus may calculate the current amount consumed for the reception operation up to now and the current amount consumed for the transmission operation up to now and calculate the total operation current consumption amount by adding the calculated current amount consumed for the reception operation up to now to the calculating current amount consumed for the transmission operation up to now.

FIG. 6 is a dark current threshold value compensation table for explaining a dark current threshold value compensation method in accordance with a vehicle temperature according to embodiments of the present disclosure.

As shown in FIG. 6, a threshold value compensation coefficient 610 may be determined based on a current vehicle temperature. As an example, if the vehicle temperature is below zero, the threshold value compensation coefficient may be defined as 1.1 and, in this case, a compensation dark current threshold value 603 may be calculated as 1.1*Threshold obtained by multiplying the threshold value compensation coefficient by an allowed dark current threshold value Threshold. That is, if a consumption current amount up to now in a telematics terminal exceeds 110% of the allowed dark current, the state of the dark current excess prevention apparatus may transition to a protection mode.

As illustrated in FIG. 6, if a vehicle temperature 602 increases, the threshold value compensation coefficient 601 may be configured to decrease and, if the vehicle temperature 602 decreases, the threshold value compensation coefficient 601 may be configured to increase.

The example of FIG. 6 is purely exemplary, and it is apparent that a method of allocating the threshold value compensation coefficient according to the range of the vehicle temperature may be changed based on experimental data etc. for each vehicle.

FIG. 7 is a flowchart for explaining an operation of a dark current prevention apparatus in a protection mode according to embodiments of the present disclosure.

As shown in FIG. 7, in the protection mode 330, the dark current excess prevention apparatus may transmit a predetermined warning message indicating that remote start is needed to a predesignated user terminal and drive a predetermined remote start standby timer (step S701 and S702).

The dark current excess prevention apparatus may check whether remote start has been performed after receiving a remote start command from the user terminal (step S703).

If remote start has been performed, the dark current excess prevention apparatus may end the driven remote start standby timer and transition to the sleep mode 310 (step S704).

If the remote start standby timer has expired without performing remote start, the dark current excess prevention apparatus may deactivate operation of a telematics terminal (steps S705 and S706). Thus, the dark current excess prevention apparatus can prevent discharge of a vehicle battery.

If remote start is performed according to the remote start command, a charge level of a vehicle battery may increase. In this case, a dark current threshold value for judging whether a dark current is exceeded may be dynamically changed based on the charge level of the battery. Accordingly, the dark current excess prevention method according to embodiments of the present disclosure can accurately determine whether the dark current is exceeded by adaptively compensating for a dark current threshold value according to a current charge level of the vehicle battery.

As an example, a charge level of the vehicle battery after remote start is performed may be calculated by multiplication of a remote start maintenance time and a battery charge rate. For example, a unit of the remote start maintenance time may be minutes and, in this case, the battery charge rate may be "mAh/minute".

Accordingly, the present disclosure provides a dark current excess prevention method in a telematics terminal and an apparatus therefor that can accurately determine whether a dark current is exceeded through calculation of a consumption power in real-time in the telematics terminal. Further, the dark current excess prevention method and apparatus therefor can accurately determine whether a dark current is exceeded by adaptively calculating a consumption power in real-time according to a vehicle temperature condition. The present disclosure can also maximize a vehicle remote controllable time by accurately judging whether a dark current is exceeded. Additionally, a telematics terminal according to the present disclosure can prevent battery discharge by requesting that a user terminal perform remote start upon judging that a dark current is exceeded.

The effects that can be achieved through the present disclosure are not limited to what has been particularly described hereinabove and other advantages not described herein will be more clearly understood by those skilled in the art from the above detailed description.

Those skilled in the art will appreciate that the present disclosure may be embodied in other specific forms than those set forth herein without departing from the spirit and essential characteristics of the present disclosure. The above description is therefore to be construed in all aspects as illustrative and not restrictive. The scope of the disclosure should be determined by reasonable interpretation of the appended claims and all changes coming within the equivalency range of the disclosure are intended to be embraced in the scope of the disclosure.

What is claimed is:

1. A dark current excess prevention method for use in a telematics terminal installed in a vehicle, the method comprising:
    providing a sleep mode where the telematics terminal is in a waiting status or receives a packet data from an external device and an active mode where the telematics terminal transmits to, and/or receives from, the external device another packet data;
    monitoring and calculating a current consumption amount from a starting time of the sleep mode up to a transition time from the sleep mode to the active mode;
    determining whether the calculated current consumption amount exceeds a predetermined dark current reference value; and
    determining that a dark current is exceeded when the calculated current consumption amount exceeds the dark current reference value.

2. The dark current excess prevention method according to claim 1, wherein the current consumption amount is further calculated by combining a current amount consumed for all of reception operations up to the present time after the starting time of the sleep mode and a current amount consumed for all of transmission operations during the active mode.

3. The dark current excess prevention method according to claim 2, wherein the current amount consumed for all of the reception operations is calculated based on a precalculated average consumption current for each reception operation.

4. The dark current excess prevention method according to claim 2, wherein the current amount consumed for all of the transmission operations is calculated by multiplying a number of transmission operations by an average current amount consumed each transmission operation.

5. The dark current excess prevention method according to claim 1, further comprising:
    transitioning to a protection mode when it is determined that the dark current is exceeded; and
    transmitting a predetermined warning message indicating that remote start is needed to a predesignated user terminal in the protection mode.

6. The dark current excess prevention method according to claim 5, further comprising:
    driving a predetermined remote start standby timer after transmitting the warning message; and
    ceasing an overall operation of the telematics terminal when a remote start command is not received from the user terminal before expiry of the remote start standby timer.

7. The dark current excess prevention method according to claim 6, further comprising:
    performing the remote start upon receiving the remote start command,
    wherein the transition to the active mode is performed when the remote start is completed.

8. The dark current excess prevention method according to claim 1, further comprising:
sensing a temperature of the vehicle,
wherein the dark current reference value is dynamically compensated for based on the sensed temperature of the vehicle.

9. The dark current excess prevention method according to claim 8, wherein the dark current reference value decreases when the sensed temperature of the vehicle increases, and the dark current reference value increases when the sensed temperature of the vehicle decreases.

10. The dark current excess prevention method according to claim 1, further comprising:
calculating a battery charge level of the vehicle,
wherein the dark current reference value is determined based on the battery charge level of the vehicle.

11. A dark current excess prevention apparatus installed in a vehicle comprising:
a communication unit configured operate in a sleep mode in the vehicle where the communication unit is in a waiting status or receives a packet data from an external device and an active mode where the communication unit transmits to, and/or receives from, the external device another packet data; and
a controller configured to monitor and calculate a current consumption amount in the vehicle from a starting time of the sleep mode up to a transition time from the sleep mode to the active mode, determine whether the calculated current consumption amount exceeds a predetermined dark current reference value, and determine that a dark current is exceeded when the calculated current consumption amount exceeds the dark current reference value.

12. The dark current excess prevention apparatus according to claim 11, wherein the current consumption amount is further calculated by combing a current amount consumed for all of reception operations up to the present time after the starting time of the sleep mode and a current amount consumed for all transmission operations during the active mode.

13. The dark current excess prevention apparatus according to claim 12, wherein the current amount consumed for all of the reception operations is calculated based on a precalculated average consumption current for each reception operation.

14. The dark current excess prevention apparatus according to claim 12, wherein the current amount consumed for all of the transmission operations is calculated by multiplying a number of transmission operations by an average current amount consumed for each transmission operation.

15. The dark current excess prevention apparatus according to claim 11, wherein the controller is further configured to transition to a protection mode when it is determined that the dark current is exceeded and transmit a predetermined warning message indicating that remote start is needed to a predesignated user terminal in the protection mode.

16. The dark current excess prevention apparatus according to claim 15, further comprising:
a timer driving a predetermined remote start standby timer after the warning message is transmitted,
wherein the controller is further configured to stop an overall operation of a telematics terminal when a remote start command is not received from the user terminal before expiry of the remote start standby timer.

17. The dark current excess prevention apparatus according to claim 16, wherein the controller is further configured to initiate performance of the remote start upon receiving the remote start command and transition to the active mode upon completing remote start.

18. The dark current excess prevention apparatus according to claim 11, further comprising:
a temperature sensor sensing a temperature of the vehicle,
wherein the controller is further configured to dynamically compensate for the dark current reference value based on the sensed temperature of the vehicle.

19. The dark current excess prevention apparatus according to claim 18, wherein the dark current reference value decreases when the sensed temperature of the vehicle increases, and the dark current reference value increases when the sensed temperature of the vehicle decreases.

20. The dark current excess prevention apparatus according to claim 11, further comprising:
a charge level sensor calculating a battery charge level of the vehicle in which a telematics terminal is installed,
wherein the controller is further configured to determine the dark current reference value based on the battery charge level of the vehicle.

* * * * *